United States Patent [19]

Jessel, Jr. et al.

[11] Plant 4,505

[45] Feb. 26, 1980

[54] CHRYSANTHEMUM PLANT

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 963,851

[22] Filed: Nov. 27, 1978

[51] Int. Cl.[2] ..... A01H 5/00

[52] U.S. Cl. ..... Plt./76

[58] Field of Search ..... Plt./76

*Primary Examiner*—Robert E. Bagwill

*Attorney, Agent, or Firm*—Donald D. Jeffery

[57] ABSTRACT

A chrysanthemum plant known by the cultivar name Tempo and particularly characterized as to uniqueness by the combined characteristics of flat capitulum form; decorative capitulum type; dark lavender pink ray floret color; diameter across face of capitulum ranging from 110 to 130 mm. at maturity; uniform eight week photoperiodic flowering response to short days; tall plant height when grown as a pinched spray pot; and semi-spreading branching pattern.

9 Drawing Figures

The present invention comprises a new and distinct cultivar of *Chrysanthemum morifolium,* Ramat., hereinafter referred to by the cultivar name Tempo.

Tempo is a product of a planned breeding program which had the objective of creating new chrysanthemum cultivars with decorative capitulum type, with lavender ray floret color, with eight or nine week flowering response, and with the ability to produce commercially acceptable quality in year round pot mum programs. Such traits in combination were not present in previously available commerical cultivars.

Tempo was originated from a cross made in a controlled breeding program in Barberton, Ohio in 1974. The female parent was #73100001 (unnamed seedling), a lavender decorative originated by the present inventors from a cross between Royal Purple (unpatented; commercially available) and Mandalay (unpatented; commercially available). The male parent of Tempo was #70029002 (unnamed seedling), a lavender decorative originated by the present inventors from a cross between Snowpink (unpatented; commercially available) and Pamplemousse (unpatented; commercially available). Mandalay and Snowpink are products of the breeding program of the present inventors. Royal Purple and Pamplemousse are of parentage unknown to the present inventors.

Tempo was discovered and selected as one flowering plant within the progeny of the stated cross by Walter H. Jessel, Jr. and William E. Duffett on Nov. 18, 1975 in a controlled environment in Barberton, Ohio.

The first act of asexual reproduction of Tempo was accomplished when vegetative cuttings were taken from the initial selection in February, 1976 in a controlled environment in Barberton, Ohio, by a technician working under formulations established and supervised by Walter H. Jessel, Jr. and William E. Duffett. Horticultural examination of selected units initiated June 22, 1977 has demonstrated that the combination of characteristics as herein disclosed for Tempo are firmly fixed and are retained through successive generations of asexual reproduction.

Tempo has not been observed under all possible environmental conditions. The phenotype may vary significantly with variations in environment such as temperature, light intensity, and daylength. The observations, measurements, and comparisions describe plants grown in Barberton, Ohio and in Salinas, Calif. under greenhouse conditions which approximate those generally used in commercial practice.

The following traits have been repeatedly observed and are determined to be basic characteristics of Tempo which in combination distinguish this chrysanthemum as a new and distinct cultivar:

(1) Flat capitulum form.

(2) Decorative capitulum type.

(3) Dark lavender pink ray floret color, with minimal color oxidation.

(4) Diameter across face of capitulum ranging from 110 to 130 mm. at maturity.

(5) Uniform eight week photoperiodic flowering response to short days.

(6) Tall plant height (requiring 1-2 long day weeks prior to pinch and short days, and two applications 2500 ppm B-9 SP 14 to 21 days after the beginning of short days to attain a flowered plant height of 30 to 45 cm.).

(7) Semi-spreading branching pattern.

The accompanying photographic drawings show typical inflorescence and foliage characteristics of Tempo, with the colors being as nearly true as possible with illustrations of this type.

Sheet 1 is a color photograph of a specimen plant of Tempo.

Sheet 2 compares Tempo (right) to Royal Trophy (left).

Sheet 3 is a black and white photograph of the foliage of Tempo at three stages of growth.

Of the many commercial cultivars known to the present inventors, the most similar existing cultivars in comparison to Tempo are the cultivars Royal Trophy (U.S. Plant Pat. No. 3,549) and Pinktive (U.S. Plant Pat. No. 4,087). Reference is made to attached Chart A which compares certain characteristics of Tempo to those same characteristics of Royal Trophy and Pinktive. General comparisions are as follows:

1. In comparision to Royal Trophy, Tempo has less blue ray floret color, more spreading branching pattern, taller plant height, and shorter flowering response period. The capitulum form, the capitulum type, and the diameter across face of capitulum of Tempo are similar to those same characteristics of Royal Trophy.

2. In comparison to Pinktive, Tempo has lighter ray floret color, different capitulum form, more upright branching pattern, larger diameter across face of capitulum, and shorter flowering response period. The capitulum form and plant height of Tempo are similar to those same characteristics of Pinktive.

In the following description, color references are made to The Royal Horticultural Society Colour Chart. The color values were determined between 2:00 and 2:30 P.M. on Aug. 31, 1978 under 90 foot-candle light intensity at Salinas, Calif.

Botanical classification: *Chrysanthemum morifolium,* Ramat., cv Tempo.

I. INFLORESCENCE

A. Capitulum:
- *Form.*—Flat.
- *Type.*—Decorative.
- *Diameter across face.*—110 to 130 mm.

B. Corolla of ray florets:
- *Color (abaxial).*—78-A (immature) to 78-B to 78-C (mature).
- *Color (adaxial).*—78-C.
- *Persistence.*—Resists shatter.

C. Reproductive organs:
- *Androecium.*—Present disc florets only; scant to few; scant pollen.
- *Gynoecium.*—Present both ray and disc florets.

II. PLANT

A. General appearance: semi-spreading branching pattern; tall height.

B. Foliage:
- *Color (abaxial).*—Approximately 137-A.
- *Color (adaxial).*—Approximately 137-D.

CHART A
COMPARISON OF TEMPO, ROYAL TROPHY AND PINKTIVE

| CULTIVAR | RAY FLORET COLOR | CAPITULUM FORM AND TYPE | BRANCHING PATTERN |
|---|---|---|---|
| TEMPO | Dark Lavender Pink | Flat Decorative | Semi-Spreading |
| ROYAL TROPHY | Dark Lavender | Flat Decorative | Semi-upright |
| PINKTIVE | Purple | Semi-incurved Decorative | Spreading |

| CULTIVAR | DIAMETER ACROSS FACE OF CAPITULUM | PLANT HEIGHT | FLOWERING RESPONSE PERIOD |
|---|---|---|---|
| TEMPO | 110 to 130 mm. | Tall | 8 week |
| ROYAL TROPHY | 110 to 130 mm. | Medium | 9 week |
| PINKTIVE | 75 to 100 mm. | Tall | 9 week |

COMPARISONS MADE OF PLANTS GROWN AS PINCHED DISBUDDED POTS IN BARBERTON, OHIO AND IN SALINAS, CALIFORNIA.

We claim:

1. A new and distinct cultivar of *Chrysanthemum morifolium,* Ramat., plant known by the cultivar name Tempo and particularly characterized as to uniqueness by the combined characteristics of flat capitulum form; decorative capitulum type; dark lavender pink ray floret color, with minimal color oxidation; diameter across face of capitulum ranging from 110 to 130 mm. at maturity; uniform eight week flowering response; tall plant height; and semi-spreading branching pattern.

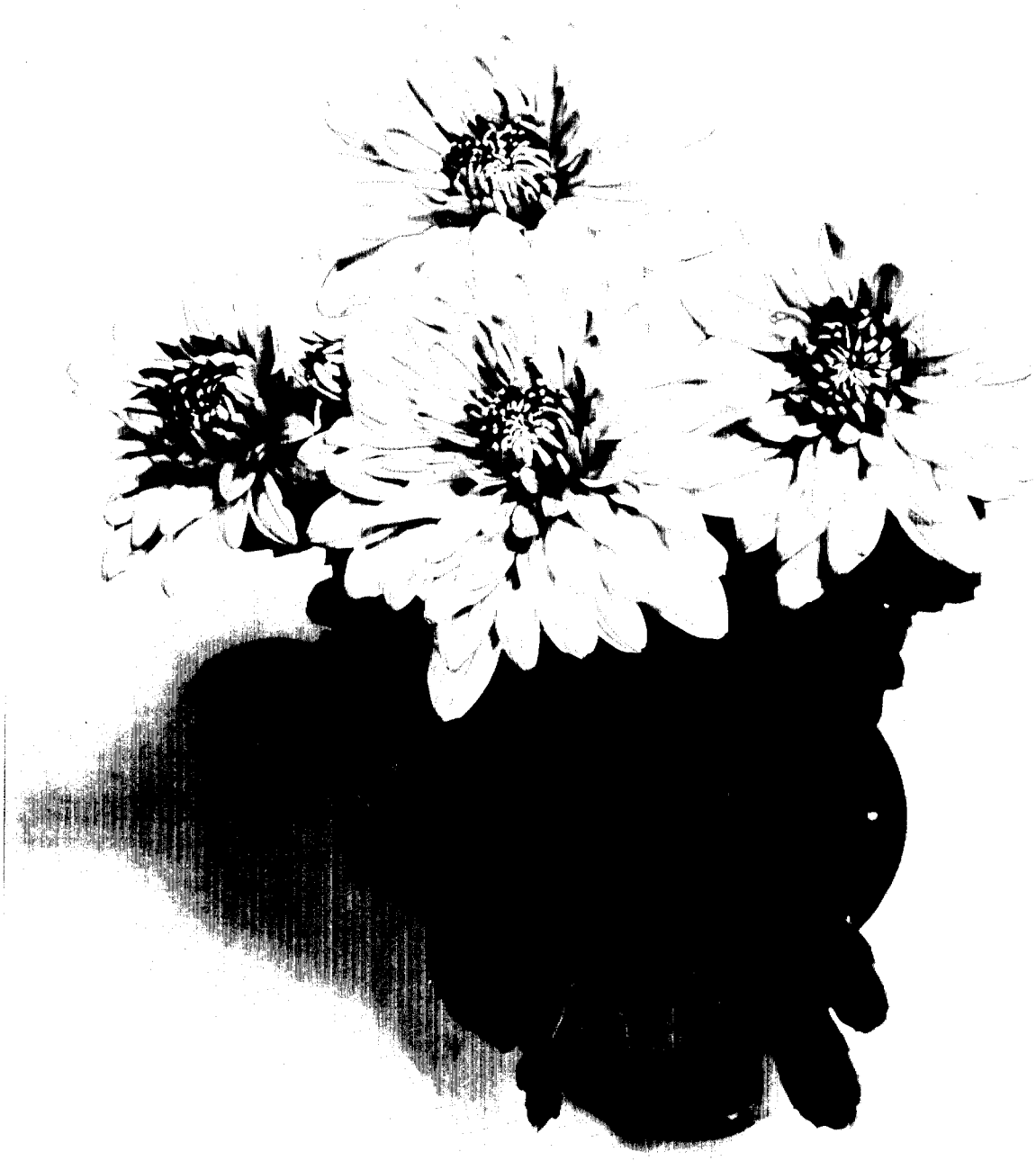

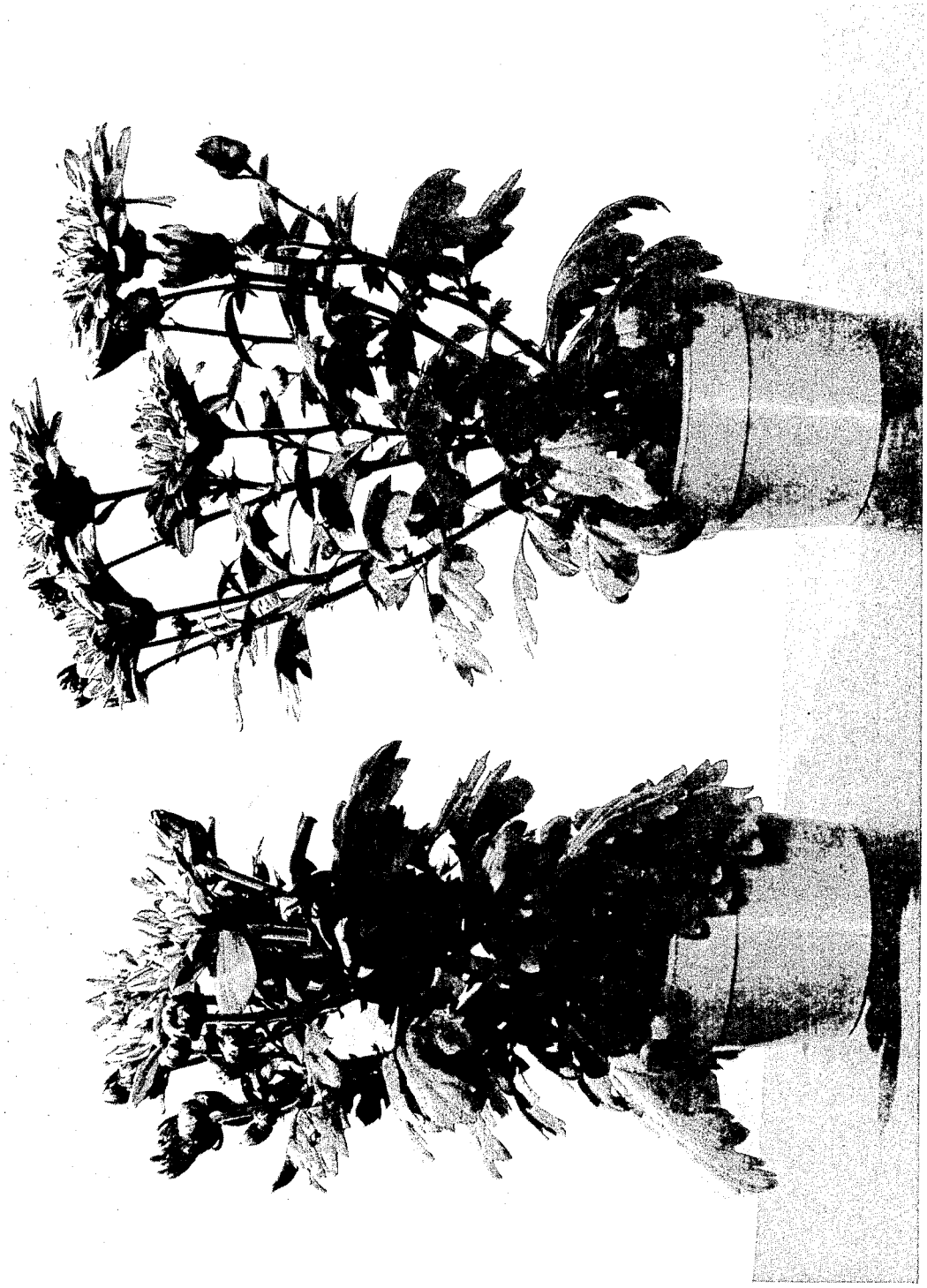

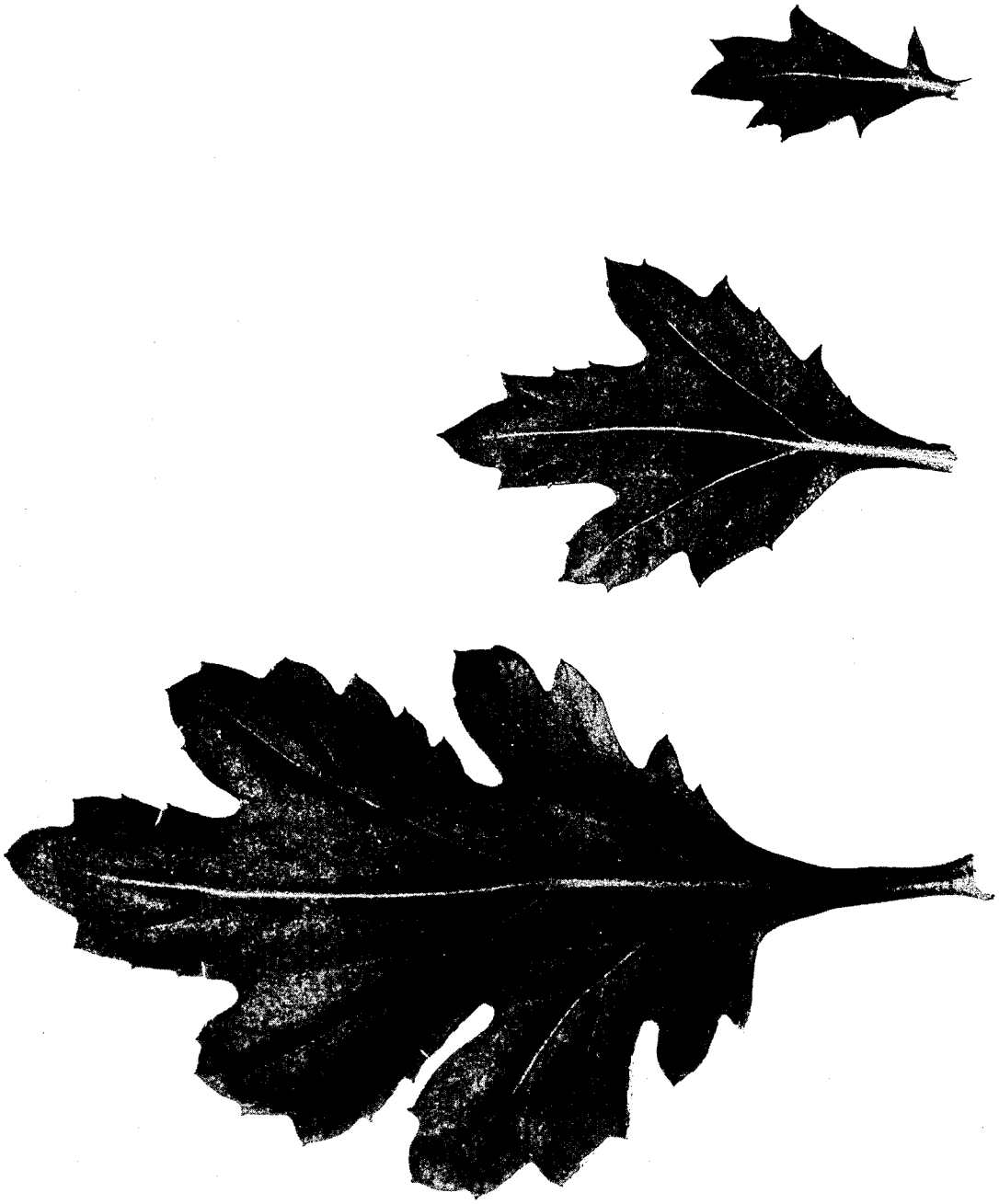

* * * * *